(12) United States Patent
Kwon et al.

(10) Patent No.: US 9,689,878 B2
(45) Date of Patent: Jun. 27, 2017

(54) ASSAY METHOD USING ENCODED PARTICLE-BASED PLATFORM

(71) Applicant: SNU R&DB FOUNDATION, Seoul (KR)

(72) Inventors: Sung Hoon Kwon, Seoul (KR); Su Eun Chung, Seoul (KR); Sung Hoon Lee, Seoul (KR); Wook Park, Seoul (KR); Young Hoon Song, Seoul (KR)

(73) Assignee: QUANTAMATRIX INC., Seoul (KR)

( * ) Notice: Subject to any disclaimer, the term of this patent is extended or adjusted under 35 U.S.C. 154(b) by 0 days.

(21) Appl. No.: 14/994,664

(22) Filed: Jan. 13, 2016

(65) Prior Publication Data

US 2016/0123987 A1     May 5, 2016

Related U.S. Application Data

(60) Division of application No. 14/153,159, filed on Jan. 13, 2014, now Pat. No. 9,267,950, which is a continuation of application No. 13/473,901, filed on May 17, 2012, now abandoned.

(30) Foreign Application Priority Data

May 17, 2011   (KR) ........................ 10-2011-0046183

(51) Int. Cl.
    *G01N 33/543*     (2006.01)
    *G01N 33/58*     (2006.01)

(52) U.S. Cl.
    CPC ..... *G01N 33/585* (2013.01); *G01N 33/54313* (2013.01); *Y10T 436/143333* (2015.01)

(58) Field of Classification Search
    None
    See application file for complete search history.

(56) References Cited

U.S. PATENT DOCUMENTS

| | | | |
|---|---|---|---|
| 4,591,570 A | 5/1986 | Chang | |
| 7,550,271 B2 | 6/2009 | Patton et al. | |
| 7,709,544 B2 | 5/2010 | Doyle et al. | |
| 2003/0129654 A1 | 7/2003 | Ravkim | |
| 2004/0013569 A1 | 1/2004 | Balkus et al. | |
| 2006/0134644 A1 | 6/2006 | Hartel et al. | |
| 2007/0166810 A1 | 7/2007 | Bobrow et al. | |
| 2008/0102518 A1 | 5/2008 | Eberett | |
| 2008/0248962 A1 | 10/2008 | Kim et al. | |
| 2010/0060875 A1 | 3/2010 | Kwon et al. | |
| 2011/0058172 A1 | 3/2011 | Moon et al. | |
| 2011/0071039 A1 | 3/2011 | Kumar et al. | |
| 2011/0172110 A1 | 7/2011 | Merriman | |

FOREIGN PATENT DOCUMENTS

| | | |
|---|---|---|
| KR | 10-2010-0029962 A | 3/2010 |
| KR | 10-1004769 B1 | 1/2011 |

OTHER PUBLICATIONS

Chung S. et al. Partipetting for Multiplexed Bioassay in Microwells. Int Conference on Miniaturized Systems for Chemistry and Life Sciences 15th Oct. 2-6, 2011, published in 2012. vol. 2:1059-1061.*
Wu W. et al. Antibody Array Analysis with Label Based Detection and Resolution of Protein Size. Molecular & Proteomics 8(2)245-257, Feb. 2009.*
Kahp Y. Suh et al., High-throughput single-cell quantification using simplemicrowell-basedcell docking and programmable time-course live-cell imaging, Oct. 19, 2011.
Ali Khademhosseini et al., Cell confinement in patterned nanoliterdroplets in a microwell array by wiping, May 2010, Journal of Biomedical Materials Research Part A, pp. 547-557.
Kim H. et al. Live Lymphocyte Arrays for Biosensing. Advenced Functional Materials 16(10) 1313-1323, 2006.
Nam H. et al. Two Dimensional Nanopatterning by PDMS Relief Structures of Polymeric Colloidal Crystals. Applied Surface Science 254(16)5134-5140, Jun. 15, 2008.

\* cited by examiner

*Primary Examiner* — Ralph Gitomer
(74) *Attorney, Agent, or Firm* — Paratus Law Group, PLLC

(57) ABSTRACT

Provided is an assay method using an encoded particle-based platform. In the assay method, first, a plurality of encoded particles having codes distinguishable from one another according to kinds of included target materials are prepared. The plurality of encoded particles are provided onto a plate including a plurality of wells by pipetting, and disposed in the plurality of wells by a self-assembly method. An analyte is provided into the plurality of wells. The codes of the plurality of encoded particles disposed in the plurality of wells are decoded. The target materials of the plurality of encoded particles are released to cause a reaction between the target materials and the analyte.

8 Claims, 18 Drawing Sheets

Prior Art

ND2 9,689,878 B2

ASSAY METHOD USING ENCODED PARTICLE-BASED PLATFORM

CROSS-REFERENCE TO RELATED APPLICATION

The present application is a Divisional of U.S. patent application Ser. No. 14/153,159 (filed on Jan. 13, 2014), under 35 U.S.C. §121, which is a Continuation Application of U.S. patent application Ser. No. 13/473,901 (filed on May 17, 2012) under 35 U.S.C. §120, which claims priority to Korean Patent Application No. 10-2011-0046183 (filed on May 17, 2011) under 35 U.S.C. §119, which are all hereby incorporated by reference in their entirety.

BACKGROUND

1. Field of the Invention

The present invention relates to an assay method, and more particularly, to an assay method using an encoded particle-based platform.

2. Discussion of Related Art

Recently, techniques such as a spotting technique, a microarray technique, an electrowetting technique, an optical tweezers technique and an optoelectronic tweezers technique have been developed to research movement of an infinitesimal amount of analyte. However, in spite of the advent of these techniques, pipetting is continuously being used as an important means for analysis. Among current pipetting techniques, robotic pipetting and spotting have been improved to enable high throughput screening (HTS), thereby solving a time consumption problem of existing manual pipetting. However, HTS handling may be limited to a use for a large amount of analyte in which expensive equipment having a high user operating cost is used.

FIG. 1 schematically illustrates an existing drug assay method using pipetting. (a) of FIG. 1 shows a library containing different drugs. (b) of FIG. 1 shows a plate having a plurality of wells to which different drugs can be distributed. Referring to (a) and (b) of FIG. 1, different drugs 110 may be distributed from the library 100 including the drugs 110 to wells 130 of a plate 120 in sequence using a pipet 120. Thereafter, the drugs 110 distributed to the wells 130 of the plate 120 react with cells, which are separately provided assay targets.

A process of distributing the drugs 110 from the library 100 to the wells 130 may be performed by sequentially pipetting each of the drugs 110 selected from the library 100 into the corresponding well 130 one by one. As an example, when a plurality of plates 120 having a plurality of wells 130 are provided and there are 100K different kinds of drugs 110 in the library 100, the process may be carried out by performing pipetting into 100K wells 130 100K times. At this time, the wells 130 of the plate 120 can be given addresses, and kinds of drugs 110 respectively pipetted into the wells 130 having the designated addresses may be determined. The number of pipetting operations may increase in proportion to kinds of drugs 110 contained in the library 100, and thus may be a temporal and financial burden when the process of distributing the drugs 110 to the wells 130 of the plate 120 is performed.

SUMMARY OF THE INVENTION

The present invention is directed to a method of providing a plurality of particles including a plurality of target materials into wells for analysis in an economical method.

The present invention is also directed to a method of providing encoded particles including drugs into wells for analysis in an economical method.

According to an aspect of the present invention, there is provided an assay method using an encoded particle-based platform, including: preparing a plurality of encoded particles having codes distinguishable from one another according to kinds of included target materials; providing the plurality of encoded particles onto a plate including a plurality of wells by pipetting, and disposing the plurality of encoded particles in the plurality of wells by a self-assembly method; providing an analyte into the plurality of wells; decoding the codes of the plurality of encoded particles disposed in the plurality of wells; and releasing the target materials of the plurality of encoded particles to cause a reaction between the target materials and the analyte.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
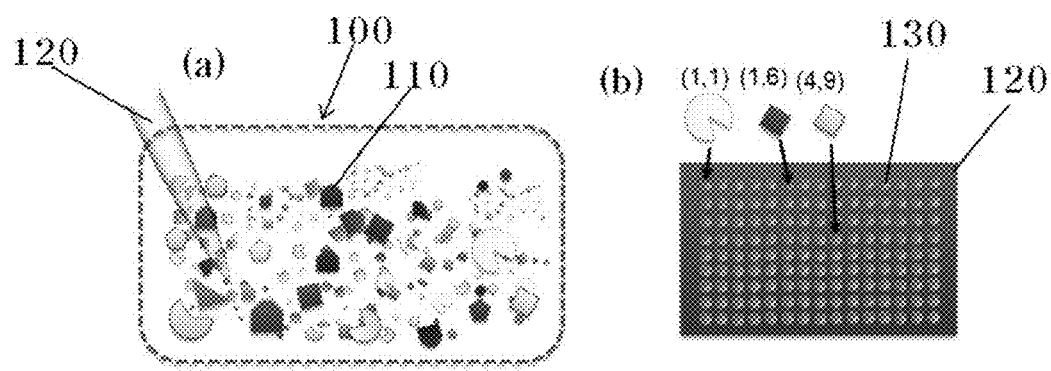
FIG. 1 schematically illustrates an existing drug assay method using pipetting.

Hereinafter, exemplary embodiments of the present invention will be described in detail below with reference to the accompanying drawings. However, the present invention is not limited to the exemplary embodiments disclosed below, but can be implemented in various forms. These exemplary embodiments are provided so that this disclosure will be thorough and complete, and will fully convey the scope of this disclosure to those of ordinary skill in the art. In the drawings, the widths and thicknesses of elements may be exaggerated for clarity. Overall description of the drawings is made from an observer's viewpoint. When an element is referred to as being "on" another element, it can be directly on the other element or intervening elements may be present. Also, it will be apparent to those of ordinary skill in the art that various modifications may be made without departing from the spirit of the present invention. Like numbers refer to like elements throughout the description of the drawings.

Meanwhile, terminology used herein will be understood as follows. Although the terms "first," "second," etc. may be used herein to describe various elements, these elements should not be limited by these terms. These terms are only used to distinguish one element from another. For example, a first element could be termed a second element, and, similarly, a second element could be termed a first element.

As used herein, the singular forms are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof. It should also be noted that in some alternative implementations, the processes noted in the blocks may occur out of the order noted in the flowcharts, unless the context clearly indicates a specific order. In other words, respective processes may be executed in a specified order, executed substantially concurrently, or executed in the reverse order.

Figure 2:
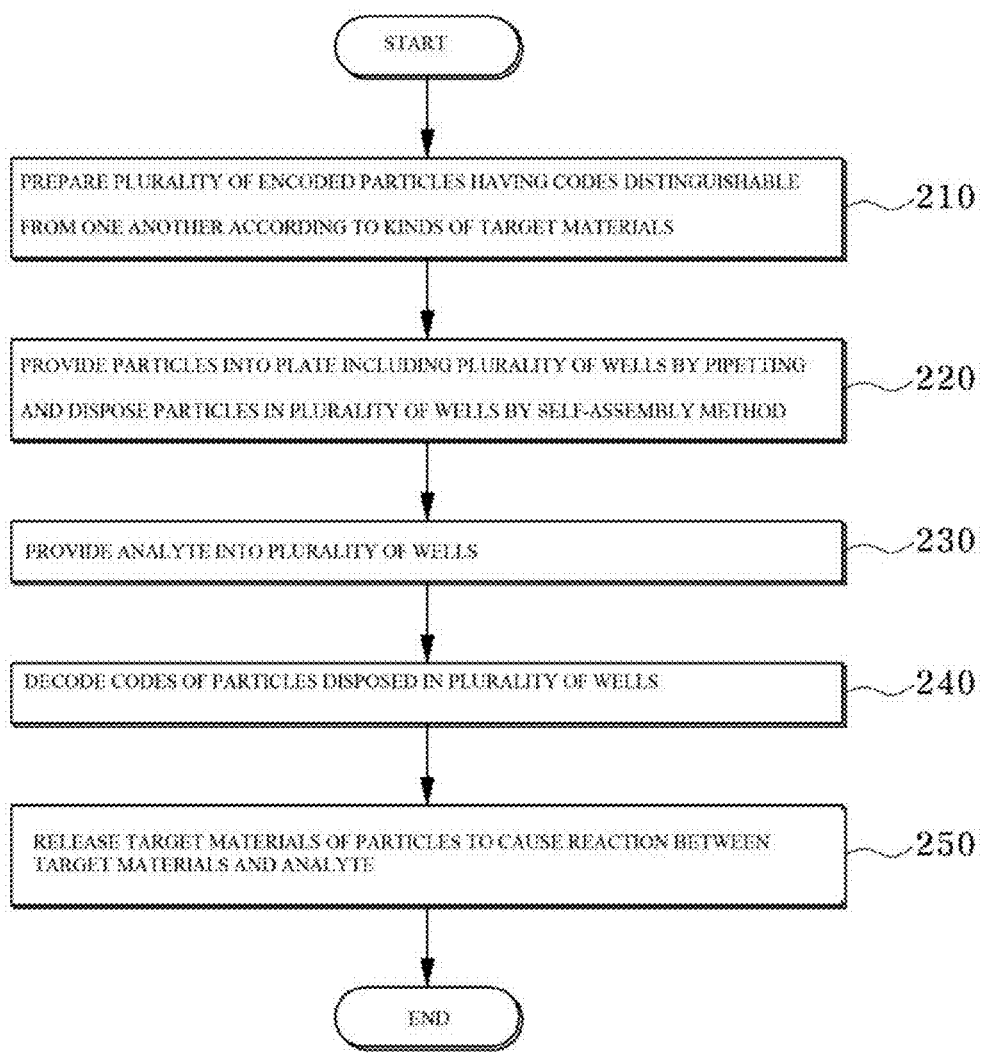
FIG. 2 is a flowchart illustrating an assay method using an encoded particle-based platform according to an exemplary embodiment of the present disclosure.
Figure 3:
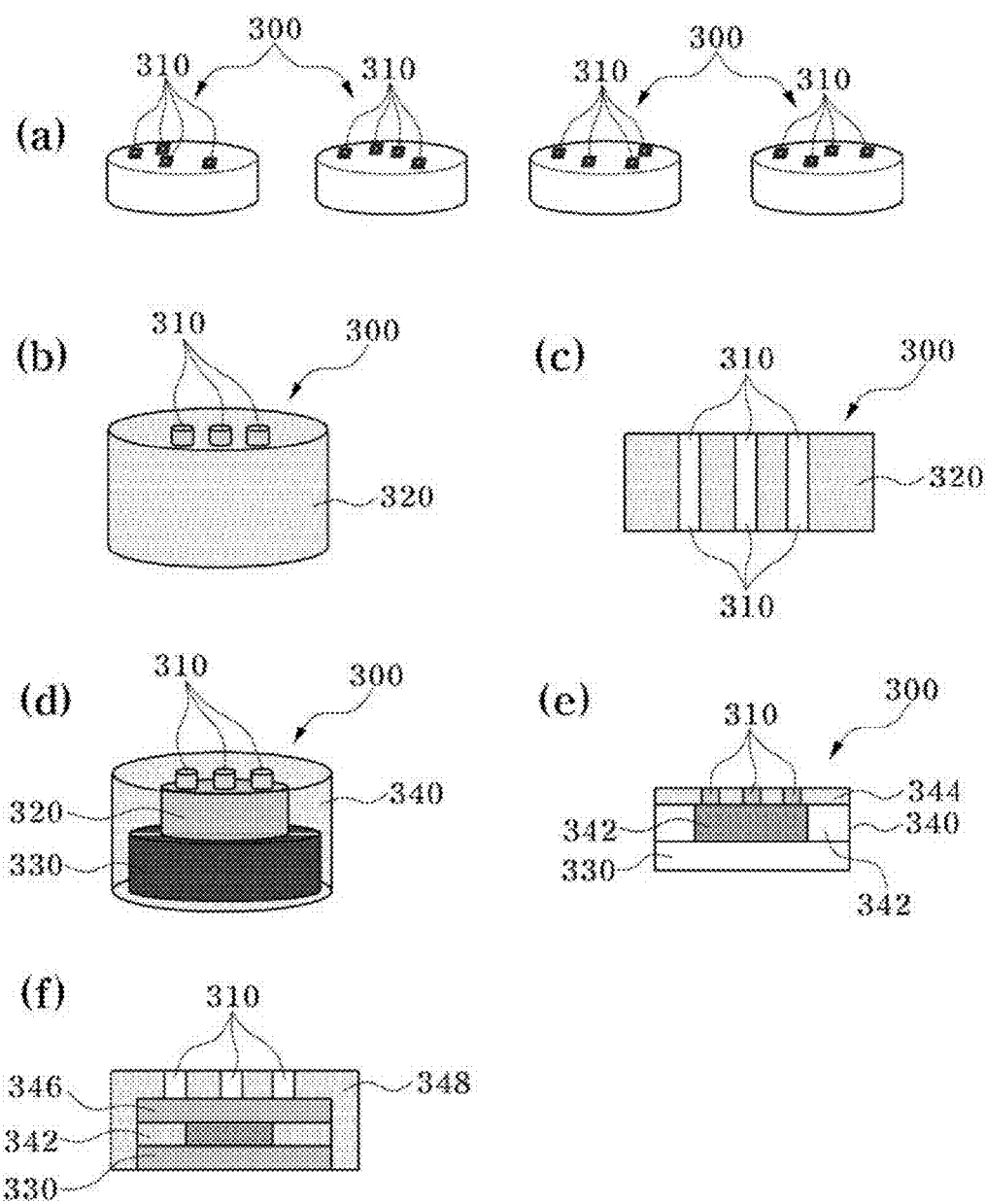
FIGS. 3 to 5 are diagrams schematically showing encoded particles according to an exemplary embodiment of the present disclosure.
Figure 4:
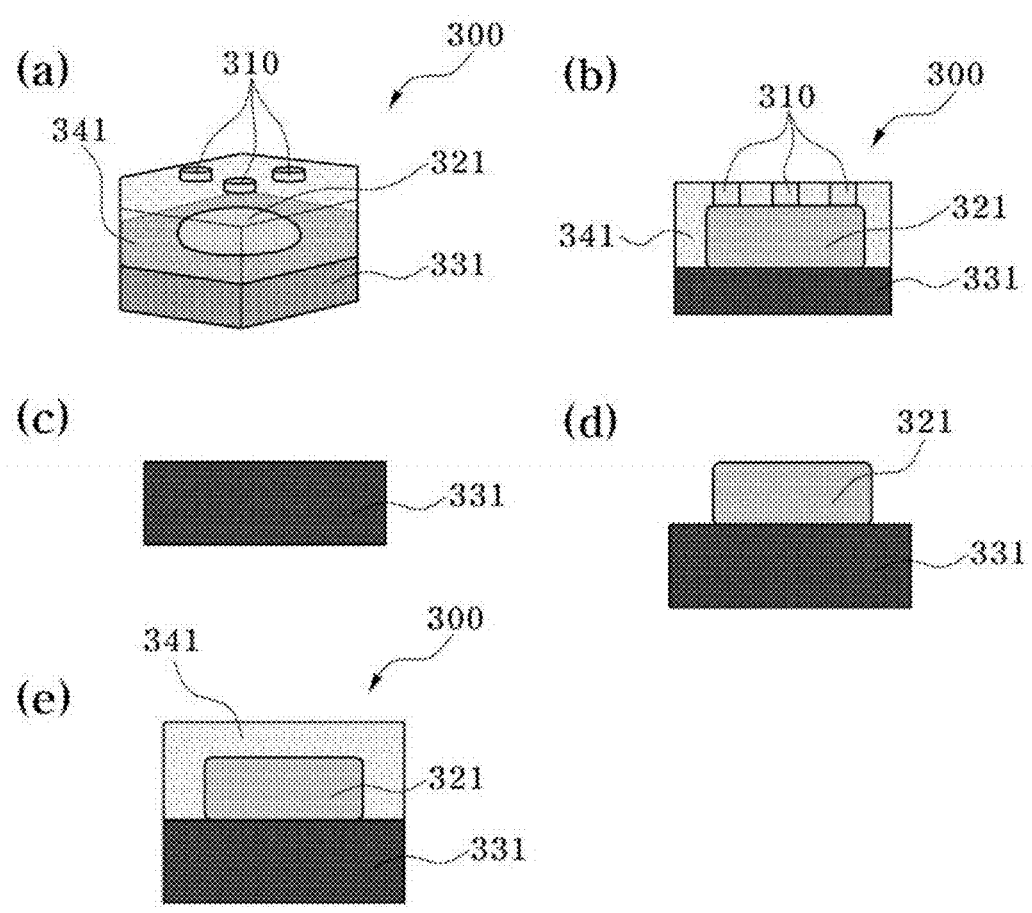
Figure 5:
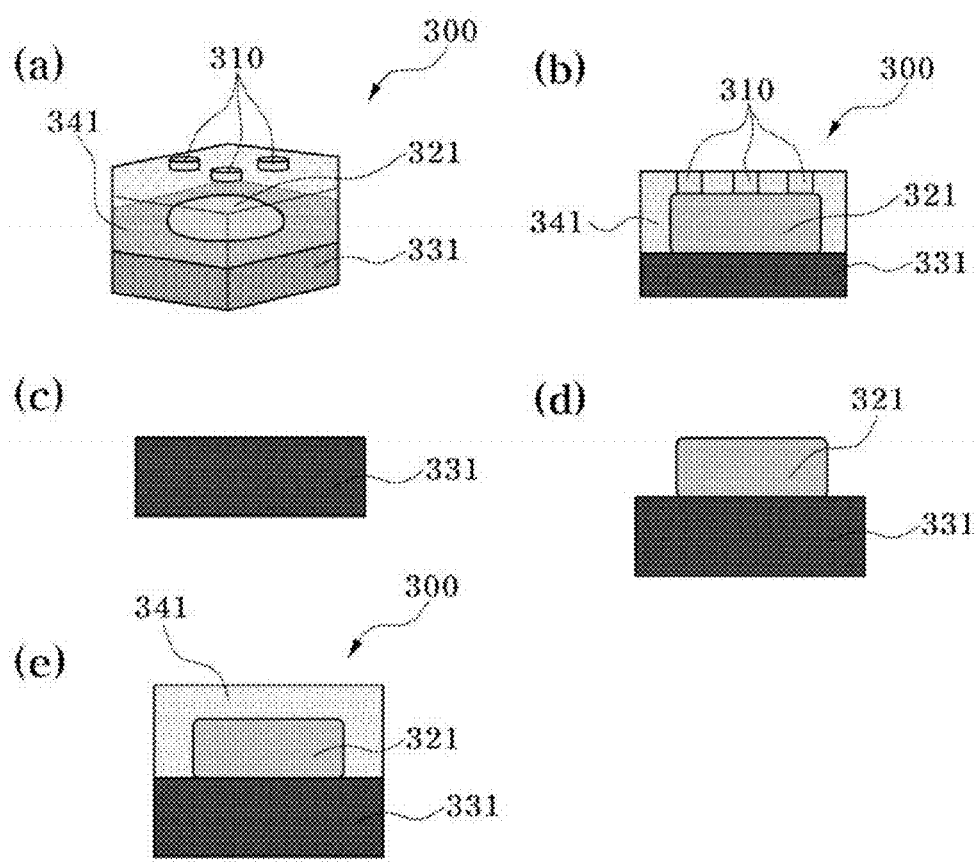

FIG. 2 is a flowchart illustrating an assay method using an encoded particle-based platform according to an exemplary embodiment of the present disclosure. FIGS. 3 to 5 are diagrams schematically showing encoded particles according to an exemplary embodiment of the present disclosure. FIGS. 6 to 18 are diagrams schematically illustrating an assay method using an encoded particle-based platform according to an exemplary embodiment of the present disclosure. Specifically, (a) of FIG. 3 schematically shows a plurality of encoded particles according to an exemplary embodiment of the present disclosure. (b) and (c) of FIG. 3 are a perspective view and a cross-sectional view of an encoded particle according to another exemplary embodiment of the present disclosure. (d) to (f) of FIG. 3 are a perspective view and a cross-sectional view of an encoded particle according to the other exemplary embodiment of the present disclosure. (a) and (b) of FIG. 4 are a perspective view and a cross-sectional view of an encoded particle according to still another exemplary embodiment of the present disclosure. (c) to (e) of FIG. 4 are diagrams schematically illustrating a method of fabricating an encoded particle according to the still other exemplary embodiment of the present disclosure. (a) and (b) of FIG. 5 are a perspective view and a cross-sectional view of an encoded particle according to yet another exemplary embodiment of the present disclosure. (c) to (g) of FIG. 5 are diagrams schematically illustrating a method of fabricating an encoded particle according to the yet other exemplary embodiment of the present disclosure. Referring to a block 210 of FIG. 2, a plurality of encoded particles having codes distinguishable from one another according to kinds of target materials are prepared. The target materials may include, for example, a chemical material, such as a drug, or at least one biological material, such as cells, molecules, protein, bacteria, deoxyribonucleic acid (DNA), and ribonucleic acid (RNA), and may react with a predetermined analyte. One or both of the chemical material and the biological material may be applied. Likewise, the analyte may include, for example, a chemical material, such as a drug, or at least one biological material, such as cells, molecules, protein, bacteria, DNA, and RNA. Referring to (a) to (f) of FIG. 3, a plurality of encoded particles 300 may include a plurality of the same or different target materials, respectively. Codes 310 of the encoded particles 300 may allow the target materials respectively included in the encoded particles 300 to be distinguished from one another. The encoded particles 300 may be in the form of, for example, hydrogel in which water is the distribution medium. For example, according to the target materials, one million or more different codes 310 may be generated.

Referring to (b) and (c) of FIG. 3, in a process of forming the particles 300 including the target materials, first, a polymer and the target materials are separately prepared. The polymer and the target materials are mixed together. The mixed polymer and target materials solidify into polymer structures 315 in which the target materials are included in the polymer. In this way, the particles 300 formed of the polymer structures 315 including the target materials may be formed. Specifically, in the process of forming the particles 300 including the target materials, the polymer and the target materials are separately prepared and mixed to form solutions in a resin form. Then, the mixed solutions in the resin form may be solidified to form the particles 300. In some other exemplary embodiments, the process of forming the particles including the target materials may be performed using a polymer that does not dissolve the target materials at a predetermined temperature or above but dissolves the target materials below the predetermined temperature. For example, a polymer having the aforementioned characteristic is poly-N-isopropylacrylamide (PNIPAAM), which is insoluble in a predetermined drug at about 32° C. or above and soluble in the predetermined drug below about 32° C. Thus, the PNIPAAM dissolved in the predetermined drug below about 32° C. is mixed with a polymer, such as polyethylene glycol-diacrylate (PEG-DA), to produce a composite in a resin form. Then, the mixed composite is solidified to form the particles. As an example of the solidification process, an optical hardening process using ultraviolet (UV) light, etc. may be performed.

In the process of forming particles including the target materials according to still other exemplary embodiments, a polymer is provided first, and solidified to form preliminary particles. Then, the target materials are injected into the preliminary particles to form the particles. For example, the preliminary particles are immersed in a bath of the target materials such that the target materials can be absorbed in polymer matrices of the preliminary particles.

In some exemplary embodiments, when the solutions in the resin form in which the target materials and the polymer are mixed are solidified to fabricate the particles, or the target materials are absorbed in the preliminary particles to fabricate the particles, a process of solidifying the formed particles by lyophilization may be additionally performed. The solidifying process may effectively cause the target materials to remain in the particles. Since it is possible to prevent a drug in a particle from diffusing out of the particle, a probability that drugs of a plurality of particles will be mixed together is lowered.

In some other exemplary embodiments, when the solutions in the resin form in which the target materials and the polymer are mixed are solidified to fabricate the particles, or the target materials are absorbed in the preliminary particles to fabricate the particles, structures of the particles may be formed and then coated with silica. The silica coating may effectively cause the target materials to remain in the particles.

When the solutions in the resin form in which the target materials and the polymer are mixed are solidified to fabricate the particles, or the target materials are absorbed in the preliminary particles to fabricate the particles, a photocurable polymer may be applied. Shapes and structures of the particles may be determined by optically patterning the photocurable polymer. As an example of the optical patterning method, optofluidic lithography disclosed in Korean Patent Registration No. 10-1004769, and flow lithography and polymerization disclosed in U.S. Pat. No. 7,709,544 may be used, and technology of these patents may be incorporated in the technology of the present disclosure.

Referring to (d) and (e) of FIG. 3, the particles 300 may have a target material layer 320 including the target materials, and a first polymer layer 330 and a second polymer layer 340 functioning as sealing layers that enclose the target material layer 320. Various methods of coding the particles 300 will be described later. The first polymer layer 330 and the second polymer layer 340 may be formed of, for example, a polymer material, but are not limited to the material. In a process of forming the particles 300 including the target materials according to an exemplary embodiment, a first fluidic polymer is provided first, and solidified to form the first polymer layer 330. A fluidic polymer including the target materials is provided on the first polymer layer 330 and solidified to form the target material layer 320. For example, the fluidic polymer absorbs and includes the target materials therein. A second fluidic polymer is provided on the target material layer 320 and solidified to form the second polymer layer 340 that seals the target material layer 320. The particles 300 may be fabricated by performing a coding process on the first polymer layer 330 and the second polymer layer 340.

In other exemplary embodiments, solutions in the resin form in which a polymer and the target materials are mixed are provided on the first polymer layer 330. The mixed solution in the resin form is solidified to form the target material layer 320. The second polymer layer 340 that seals the target material layer 320 is formed. To form the first and second polymer layers 330 and 340, the above-described method of providing a fluidic polymer and solidifying the fluidic polymer may be used.

In the cross-sectional view shown in (e) of FIG. 3, the second polymer layer 340 may be classified into a sidewall 342 outside the target material layer 320 and an upper surface 344 on the target material layer 320. The sidewall 342 may surround the outer surface of the target material layer 320 to isolate the target materials from the outside. The upper surface 344 may be used as a portion in which the codes 310 are generated to distinguish the particles 300 from one another. In the cross-sectional view shown in (f) of FIG. 3, the second polymer layer 340 may be classified into a sidewall 342 outside the target material layer 320 and a first upper surface 346 and a second upper surface 348 on the target material layer 320. The sidewall 342 and the first upper surface 346 may surround the outer surface of the target material layer 320, thereby functioning to isolate the target materials from the outside of the particles 300. The second upper surface 348 encloses the first polymer layer 330, the sidewall 342 and the first upper surface 346, thereby functioning to isolate them from the outside of the particles 300. Also, the codes 310 may be generated in a part of the second upper surface 348 to distinguish the particles 300 from one another.

The particles may be structures having a predetermined width and height as shown in (d) and (e) of FIG. 3. In an exemplary embodiment, a method of forming the target material layer, the first polymer layer 330, and the second polymer layer 340 may be performed by optically patterning the first and second polymer or the fluidic polymer including the target materials. As an example of the optical patterning method, optofluidic lithography disclosed in Korean Patent Registration No. 1004769, and flow lithography and polymerization disclosed in U.S. Pat. No. 7,709,544 may be used, and technology of these patents may be incorporated in the technology of the present disclosure.

In other exemplary embodiments, referring to (a) and (b) of FIG. 4, a particle 300 may have a first polymer layer 331, a target material layer 321, and a second polymer layer 341. Various methods of forming a code 310 in the particle 300 will be described later. Referring to (c) to (e) of FIG. 4, in a process of forming the particle 300 including the target material according to one exemplary embodiment, the first polymer layer 331 is formed first as shown in (c) of FIG. 4. The first polymer layer 331 may include a polymer, for example, perfluoro polyether (PFPE). As shown in (d) of FIG. 4, the target material is dropped on the first polymer layer 331 in the form of droplets, thereby forming the target material layer 321. The target material is selected to show hydrophobicity on the first polymer layer 331. The target material layer 321 may be disposed, for example, in the form of droplets. As shown in (e) of FIG. 4, the second polymer layer 341 that seals the target material layer 321 is formed on the target material layer 321. The particle 300 formed in this way may be a structure having a predetermined width and height as shown in (a) and (b) of FIG. 4.

A method of forming the first and second polymer layers 331 and 341 may be performed by providing a fluidic polymer and solidifying the fluidic polymer. The first and second polymer layers 331 and 341 may be formed of, for example, a photocurable polymer. Shapes and structures of the first and second polymer layers 331 and 341 may be formed by, for example, patterning the photocurable polymer through an optical method. Specifically, the first and second polymer layers 331 and 341 may be hydrophobic polymer layers, for example, PFPE or epoxy layers. In this way, the first and second polymer layers 331 and 341 may function to seal the target material in a liquid form therein such that the target material can be included in the particle 300 for a long time. As an example of a method of optically patterning the photocurable polymer, optofluidic lithography disclosed in Korean Patent Registration No. 1004769, and flow lithography and polymerization disclosed in U.S. Pat. No. 7,709,544 may be used, and technology of these patents may be incorporated in the technology of the present disclosure.

In a method of forming the target material layer 321 and the second polymer layer 341 according to another example embodiment, a hydrophilic polymer layer, such as a PEG-DA layer, is formed on the first polymer layer 331 first. Then, the formed polymer layer is made to absorb the target material, thereby forming the target material layer 321. For example, a structure including the hydrophilic polymer layer and the hydrophobic first polymer layer 331 is immersed in a bath of the target material, and the target material is made to be absorbed in a matrix of the hydrophilic polymer layer, such that the target material layer 321 can be formed. To help the target material to be absorbed in the polymer layer, a known mechanical process for forming a vortex, etc. may be added. Subsequently, the second polymer layer 341 that seals the target material layer 321 is formed.

In some other exemplary embodiments, as shown in (a) and (b) of FIG. 5, a particle 300 may have a first polymer layer 331, a first structure 333, a second structure 335, a third structure 337, a target material layer 321, and a second polymer layer 341. Various methods of coding the particle 300 will be described later. In a process of forming the particle 300, the first polymer layer 331 is formed first as shown in (c) of FIG. 5. The first polymer layer 331 may include a hydrophobic polymer, for example, PFPE. Referring to (d) of FIG. 5, the first structure 333 may be formed of a hydrophobic polymer material, such as PFPE, in the form of a wall on the first polymer layer 331. For example, the first structure 333 may be formed by coating an upper surface of the first structure 333 with a hydrophobic polymer having photocurability and optically patterning and solidifying only a portion of the hydrophobic polymer corresponding to the wall. The structure 333 in the form of a wall may be formed into a structure, for example, a bank, along the edge of the first polymer layer 331. Referring to (e) of FIG. 5, the second structure 335 is formed of a hydrophilic polymer, such as PEG-DA, in the first polymer layer 331 on the first structure 333. In one exemplary embodiment, the second structure 335 may be formed on a sidewall of the first structure 333. The second structure 335 may be formed by coating the upper surface of the first structure 333 with a hydrophilic polymer having photocurability and optically patterning and solidifying only a portion of the hydrophilic polymer corresponding to the sidewall. Referring to (f) of FIG. 5, the target material is provided in the structure in the form of a well formed of the first polymer layer 331 and the second structure 335. For example, the target material may be provided by dropping the target material on the first polymer layer 331 in the form of droplets, or spraying the target material on the first polymer layer 331. The target material is contained in the structure in the form of a well, which consists of the sidewall formed of the hydrophilic polymer and the bottom surface formed of the hydrophobic polymer, to form the target material layer 321. Referring to (g) of FIG. 5, the third structure 337 is formed on the target material layer 321. The third structure 337 serves to seal the target material layer 321. The third structure 337 may be distinguished from the second polymer layer 341 in which a code 310 for identifying the particle 300 is formed. The second polymer layer 341 functions to seal and isolate the first polymer layer 331, the first structure 333, and the third structure 337 from the outside, and the code 310 for identifying the particle 300 may be formed in a portion of the second polymer layer 341 on the third structure 337.

Referring back to the block 210 of FIG. 2, as an example of a method of coding the particles 300, a patterning method employing optical lithography may be used. As described above, the particles 300 may be encoded by applying a photocurable polymer to fabrication of the particles 300 and patterning the photocurable polymer through optical lithography. For example, optofluidic lithography disclosed in Korean Patent Registration No. 1004769, and flow lithography and polymerization disclosed in U.S. Pat. No. 7,709,544 may be used. However, the method of coding the particles 300 is not limited to these methods, and various known lithography methods may be employed. As an example of the method of coding the particles 300, respective marks denoting "1" and "0" are patterned to be distinguished from each other according to the degree of photocurability, such that codes can be formed on the particles 300. For example, when a digital micromirror device that does not employ a mask is used, one million or more codes of various kinds can be formed in the particles 300 including the target materials in the above-mentioned optical lithography method.

In other exemplary embodiments, a method of using magnetic ink may be employed as the method of coding the particles 300. For example, as disclosed in Korean Patent Application No. 10-2010-0029613, a photocurable material including magnetic nanoparticles is provided, and the magnetic nanoparticles are aligned by applying an external magnetic field. Then, light is applied from the outside to solidify the photocurable material. In this way, the method of using magnetic ink may be performed. Due to the strength of the magnetic field, the array of the magnetic nanoparticles may vary and emit different colors. Using such a technique, magnetic nanoparticles are aligned in the polymer structure 315 and the second polymer layers 341, 344 and 348 of the particles 300 formed of a photocurable polymer, such that the particles 300 can be color encoded. The technology of the patent may be incorporated in the technology of the present disclosure.

In still other exemplary embodiments, the method of coding the particles 300 may be performed by including fluorescent materials of various colors distinguishable from one another in the particles 300. As a method of including the fluorescent materials in the particles 300, various known techniques may be employed. A plurality of encoded particles that are fabricated to have codes distinguishable from one another according to kinds of target materials as mentioned above may be prepared.

Figure 6:
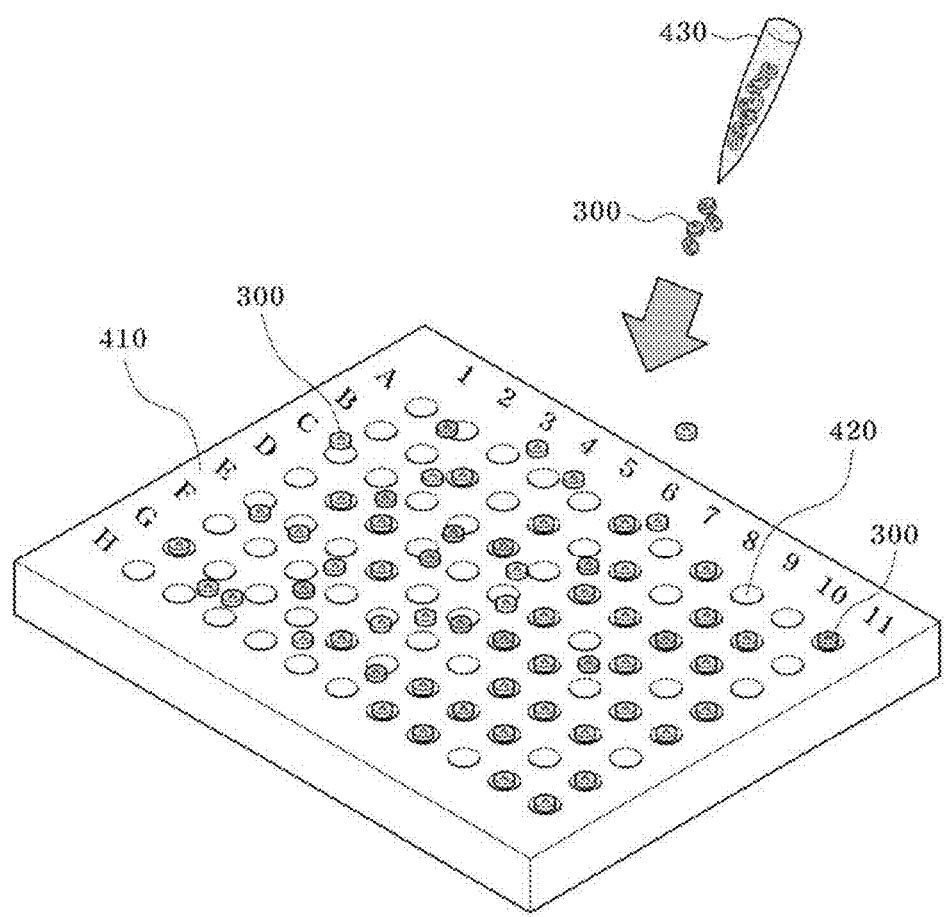
FIGS. 6 to 18 are diagrams schematically illustrating an assay method using an encoded particle-based platform according to an exemplary embodiment of the present disclosure.

Referring to a block 220, the plurality of encoded particles are provided onto a plate including a plurality of wells by pipetting, and aligned in the plurality of wells by a self-assembly method. Referring to FIG. 6 as an exemplary embodiment, particles 300 are provided onto a plate 410 including a plurality of wells 420 by pipetting. In this specification, pipetting means an action of moving the plurality of encoded particles 300 from one place to another using an instrument. The instrument may be, for example, a pipet. However, the instrument is not limited to a pipet, and may also be a tool for temporarily storing and moving the plurality of particles 300 such as a vial. In this specification, pipetting is useful and different from an existing method of using a pipet in that the respective particles 300 are not moved individually but moved all together.

The plate 410 may be manufactured using various materials including a polymer, such as polydimethylsiloxane (PDMS) and PEG-DA, glass, plastic, semiconductor, metal, ceramic, and so on. The plate 410 has the wells 420 therein and can function as a container for the particles 300. In an exemplary embodiment of the present disclosure, the plurality of encoded particles 300 may be provided onto the plate 410 by one pipetting operation. In an exemplary embodiment, the plurality of encoded particles 300 may be carried from a storage using an instrument such as the pipet 430, and then expelled from the pipet 430 to the plate 410.

The process of providing the plurality of encoded particles 300 onto the plate 410 using the pipet 430 may be performed according to types of the plurality of encoded particles 300 as follows. As shown in (d) and (e) of FIG. 3, (a) and (b) of FIG. 4, and (a) and (b) of FIG. 5, when the target material layers 320 and 321 of the plurality of encoded particles 300 are sealed by the sealing layers 330 and 340 or the first and second polymer layers 331 and 341, the plurality of encoded particles 300 may be carried using a fluid, such as an alcohol (e.g., ethyl alcohol), water, phosphate buffered saline (PBS), or an oil, as a carrier. Specifically, the plurality of encoded particles 300 may be immersed in the fluid such as ethyl alcohol, water, PBS, or an oil, and the fluid including the encoded particles 300 may be contained in the pipet 430 and carried to the plate 410. Here, the concentration of the particles 300 in the carrier may be calculated as the number of the particles 300 included in a predetermined amount of the carrier.

As shown in (b) and (c) of FIG. 3, when a particle is fabricated by solidifying a solution in the resin form in which a target material and a polymer are mixed or injecting the target material to the preliminary particle, the particle may be carried using a fluid, such as an oil, as a carrier. As an example of the oil, a volatile oil may be used, and function to protect the particle such that the target material in the solidified particle is prevented from escaping the particle during the carriage process. As in the above-described other exemplary embodiments, when the plurality of encoded particles are the particles solidified by lyophilization, the encoded particles may be carried in the form of powder without a carrier. Alternatively, the encoded particles may be carried using the fluid, such as the oil, as a carrier.

Figure 7:
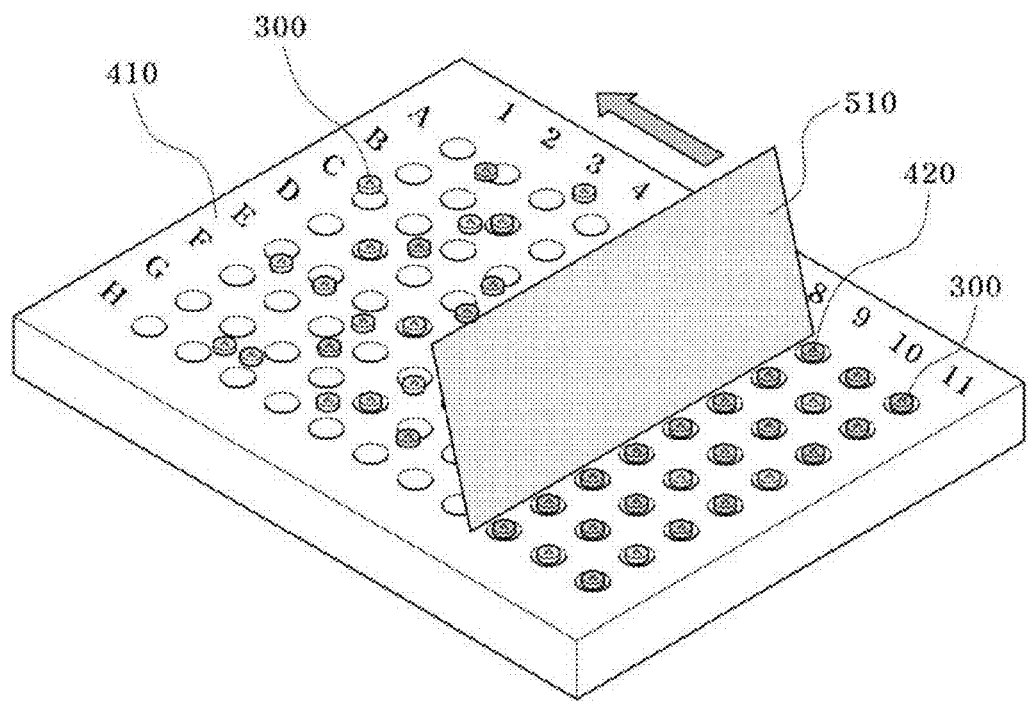

The plurality of encoded particles provided onto the plate are aligned in the plurality of wells by the self-assembly method. In this specification, the self-assembly method means a method in which the plurality of encoded particles provided onto the plate respectively move to the plurality of wells and are aligned in the wells due to a force applied from the outside to the plurality of encoded particles or a force exerted between the plurality of encoded particles and the plate. The force may be electrostatic force, capillary force, gravity, external force, and so on. FIG. 7 illustrates a method of moving the plurality of encoded particles 300 into the plurality of wells 420 by the self-assembly method according to an exemplary embodiment of the present disclosure. Referring to FIG. 7, the plurality of encoded particles 300 may be swept into the plurality of wells 420 using a structure 510. For example, at least a portion of the structure 510 may have a flat shape. The structure 510 may be manufactured using, for example, glass. However, the structure 510 is not limited to glass, but may be manufactured using various materials, such as a polymer, glass, plastic, semiconductor, metal and ceramic, as long as the materials function to move the plurality of encoded particles 300 into the plurality of wells 420. When the plurality of encoded particles 300 are carried by the fluid as in the above-described exemplary embodiments, the process of sweeping the fluid may be performed. In this case, the higher the concentration of the plurality of encoded particles 300 included in the fluid, the greater the number of encoded 300 assembled into the wells 420 at a time.

Figure 8:
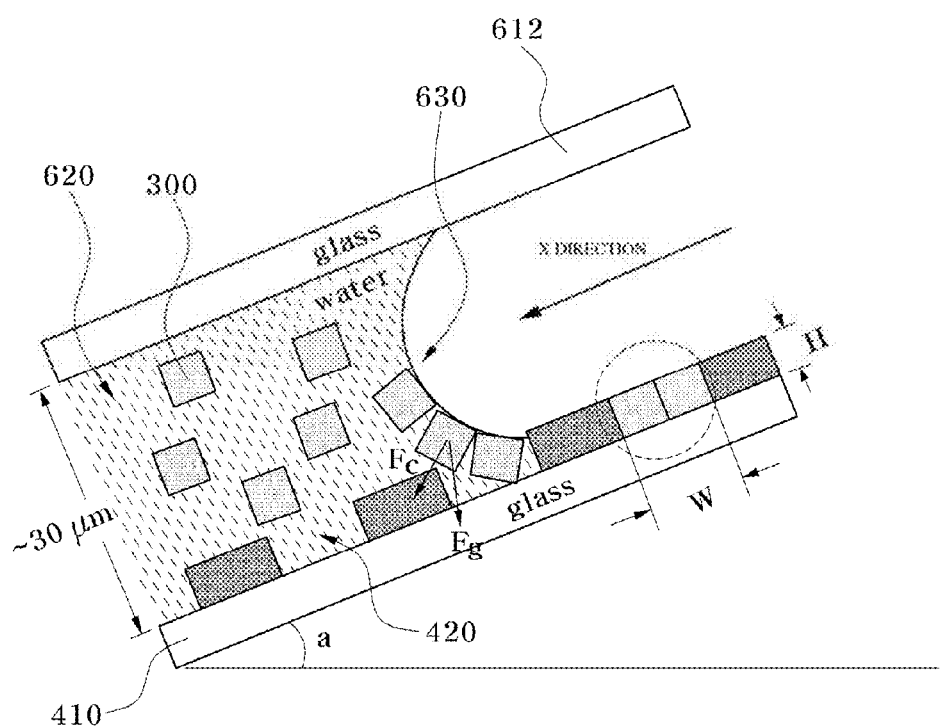

FIG. 8 illustrates a method of assembling the plurality of encoded particles into the plurality of wells by the self-assembly method according to another exemplary embodiment of the present disclosure. Referring to FIG. 8, a structure 612 is disposed substantially parallel to the plate 410. The structure 612 may be manufactured using various materials, for example, a glass, polymer, plastic, semiconductor, metal, and ceramic. For example, when the plate 410 is a glass substrate having the wells 420 of polymer patterns, the structure 412 may be a glass substrate. Between the plate 410 and the structure 612, a fluid 620 including the plurality of encoded particles 300 may be provided and made to flow in the depicted X direction. In an exemplary embodiment, the plate 410 and the structure 612 may be tilted for the flow of the fluid 620 by a predetermined angle a with respect to the flat ground. The fluid 620 flowing between the plate 410 and the structure 612 has a meniscus 630 of a semicircular shape due to a capillary force Fc, which is also exerted on the plurality of encoded particles 300 in the fluid 620. The plurality of encoded particles 300 may be inserted in the plurality of wells 420 by the capillary force Fc, gravity Fg, etc. while moving in the fluid 620. The plurality of encoded particles 300 inserted in the plurality of wells 420 may not escape from the wells 420 but may be aligned in the plurality of wells 420. To accommodate the plurality of encoded particles 300 inserted in the plurality of wells 420, sizes, such as a height H, a width W and a length, of the wells 420 may be adjusted. The drawing shows that two encoded particles 300 are aligned in one well 420. However, the present disclosure is not limited to the drawing, but may be designed such that various numbers, which are equal to or greater than one, of encoded particles 300 can be accommodated according to sizes of the wells 420.

Figure 9:
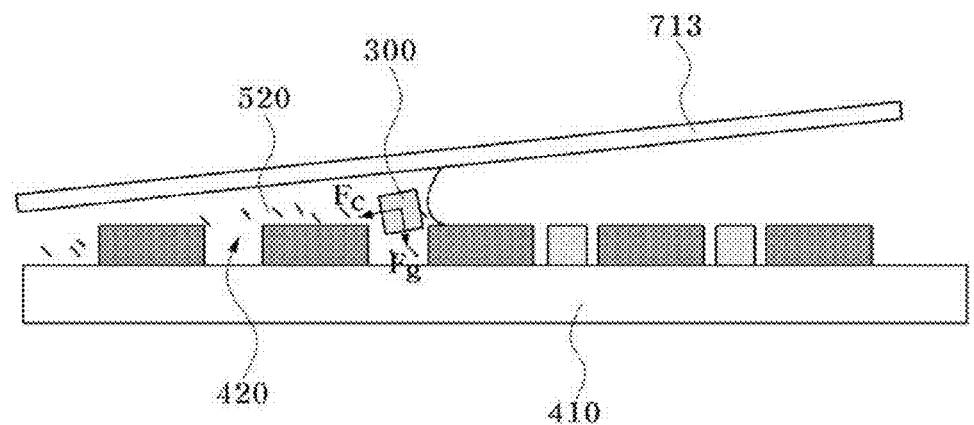

FIG. 9 illustrates a method of moving the plurality of encoded particles into the plurality of wells by the self-assembly method according to still another exemplary embodiment of the present disclosure. Referring to FIG. 9, a structure 713 is disposed to be tilted at a predetermined angle with respect to the plate 410, and a fluid 520 including the plurality of encoded particles 300 is provided between the plate 410 and the structure 713. The predetermined angle forms a space between the plate 410 and the structure 713 occupied by a predetermined number of encoded particles 300. Forces, such as the capillary force Fc and the gravity Fg, are exerted on the encoded particles 300 in the fluid 520, such that a predetermined number of encoded particles 300 can be inserted in the plurality of wells 420. The encoded particles 300 having moved into the plurality of wells 420 may be aligned in the wells 420. In some exemplary embodiments, when the fluid 520 including the encoded particles 300 is provided between the plate 410 and the structure 713, the fluid 520 is evaporated with a predetermined temperature and humidity maintained, such that the encoded particles 300 can be inserted in the wells 420.

Figure 10:
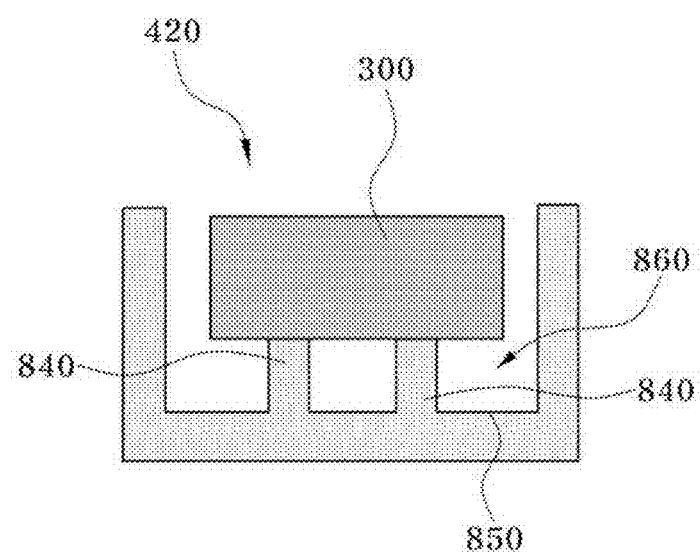

FIG. 10 is a cross-sectional view schematically showing an inside of a well 420 according to an exemplary embodiment of the present disclosure. Referring to FIG. 10, the well 420 may have at least one support 840 that supports an encoded particle 300 therein. When the encoded particle 300 is disposed on the at least one support 840 in the well 420, the well 420 may have spaces 860 between the encoded particle 300 and a bottom surface 850. In the spaces 860, an analyte 910 to be described later may be provided and disposed. In some exemplary embodiments, the support 840 may be designed to help a grinder 1210, which will be described later, to grind the encoded particle 300. Thus, a shape and structure of the support 840 may be variously designed such that the grinding function of the grinder 1210 can be efficiently performed. The support 840 functions to separate the encoded particle 300 and the analyte 910 to be described later from one another by the spaces 860. Even after the encoded particle 300 is ground or destroyed, the support 840 may physically separate the encoded and destroyed particle 300 and the analyte 910. Thus, it is possible to directly observe whether or not a reaction such as a fluorescent image occurs between the target materials and the analyte 910 without removing the encoded and destroyed particle 300. FIG. 10 shows one aspect of the well 420, but the well 420 may have various internal shapes different from that shown as long as a function of accommodating the particle 300 is maintained.

Figure 11:
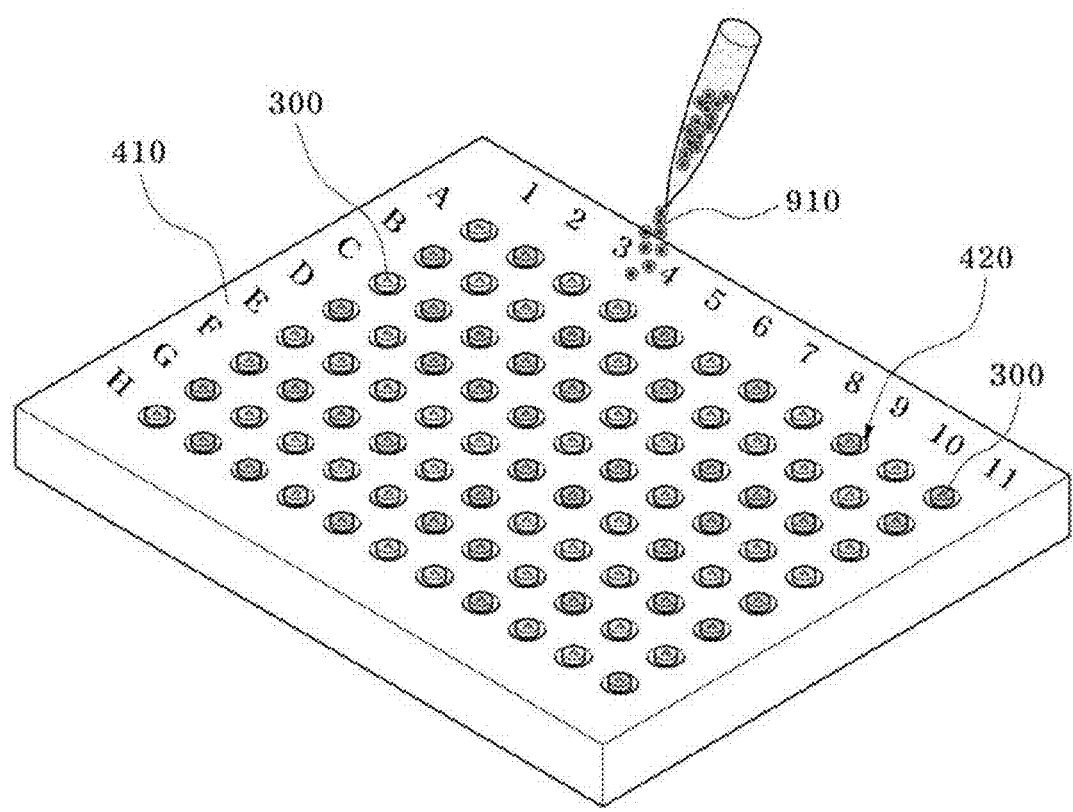

Referring to a block 230, an analyte is provided into the plurality of wells. The analyte may be, for example, a chemical material, such as a drug, or a biological material, such as cells, molecules, protein, bacteria, DNA, and RNA. The analyte may be one or more kinds. FIG. 11 is a diagram schematically illustrating a method of providing the analyte into the plurality of wells according to an exemplary embodiment of the present disclosure. As shown in the drawing, an analyte 910 may be provided into a plurality of wells 420 by pipetting. However, the method of providing the analyte 910 into the plurality of wells 420 is not limited to pipetting, but various known methods may be used. Specifically, in another exemplary embodiment, a method of moving the biological material into the wells 420 using a patterned microfluidic channel, a method of pipetting a solution including the biological material and sweeping the biological material into the wells 420 using a cover glass, etc. may be employed as the method of providing the biological material into the plurality of wells 420. The method of moving the biological material into the wells 420 using a patterned microfluidic channel is disclosed in Kahp Y. Suh et al., "High-throughput single-cell quantification using simple microwell-basedcell docking and programmable time-course live-cell imaging", 19 Oct. 2011, Lab on a Chip, Issue 1, and the method of pipetting a solution including the biological material and sweeping the biological material into the wells 420 using a cover glass is disclosed in Ali Khademhosseini et al., "Cell confinement in patterned nanoliter droplets in a microwell array by wiping", May 2010, Journal of Biomedical Materials Research Part A, 93(2), pages 547-557. The above-mentioned technology may be applied as components in an exemplary embodiment of the present disclosure. In still another exemplary embodiment, referring to FIG. 12, a plate 410 having a plurality of wells 420 in which a plurality of encoded particles 300 are disposed as shown in (a) is prepared. Mineral oil 423 may be provided in the plurality of wells 420. In an exemplary embodiment, the mineral oil 423 forms an oil layer 425 between the plurality of wells 420 as shown in (a) of FIG. 12. Also, a plate 510 having a plurality of wells 515 is separately manufactured, and the analyte 910 is disposed in the plurality of wells 515 of the separately manufactured plate 510. In an exemplary embodiment, the analyte 910 may be immersed in a medium 920 and disposed in the plurality of wells together with the medium 920. As shown in (b) of FIG. 12, the plurality of wells 515 in which the analyte 910 is disposed are combined with the plate 410 having the wells 420 in which the plurality of encoded particles 300 are disposed. At this time, the plurality of wells 515 are combined with the plate 410 such that the plurality of wells 515 and the plurality of wells 420 correspond to each other. As shown in the drawing, the oil layer 425 formed between the plurality of wells 420 may isolate the plurality of wells 420 from one another. As shown in (c) of FIG. 12, the plurality of encoded particles 300 in contact with the medium 920 release the analyte 910 in the wells 420 through a predetermined reaction.

In some exemplary embodiments, a diameter and height of the plurality of wells 515 in which the analyte 910 is disposed may be substantially the same as those of the wells 420 in which the particles 300 are disposed. Alternatively, the diameter and height of the plurality of wells 515 may be greater than those of the wells 420 in which the particles 300 are disposed to sufficiently accommodate the medium 920 including the analyte 910.

Figure 13:
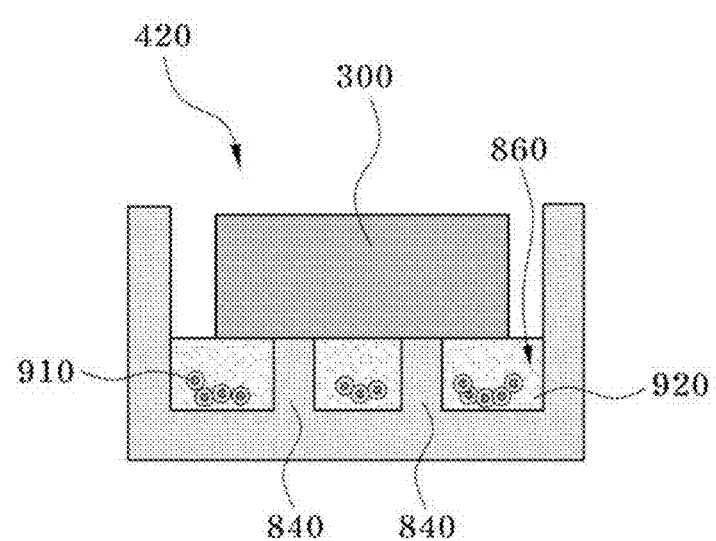

In some exemplary embodiments, as shown in FIG. 13, the analyte 910 may be disposed to be in contact with or spaced apart from the particles 300 in the plurality of wells 420. When the analyte 910 is a biological material, the analyte 910 may be provided into the plurality of wells 420 together with the medium 920. Referring to the drawing, the analyte 910 may be provided in the spaces 860 divided by the at least one support 840. As shown in the drawing, the analyte 910, which is a biological material, may be disposed in the spaces 860 in the wells 420 together with the medium 920.

Referring to a block 240, codes of the particles disposed in the plurality of wells are decoded. When the particles 300 are encoded by patterning the photocurable polymer through optical lithography according to an exemplary embodiment, a method of decoding the codes of the particles 300 may performed by decoding the patterned marks. The patterned marks may be decoded by, for example, taking an image. When the particles 300 are encoded through coloring caused by the magnetic nanoparticles or the fluorescent materials of the particles 300, the method of decoding the codes of the particles 300 may be performed by decoding colors of the magnetic nanoparticles or the fluorescent materials. The colors may be decoded by, for example, taking an image. By decoding the codes of the particles 300, the kinds of the particles 300 respectively disposed in the plurality of wells 420 of the plate 410 may be checked. Through the code decoding process of the particles 300, the kinds of the target materials reacting with the analyte 910, which will be described later, may be checked.

Figure 14:
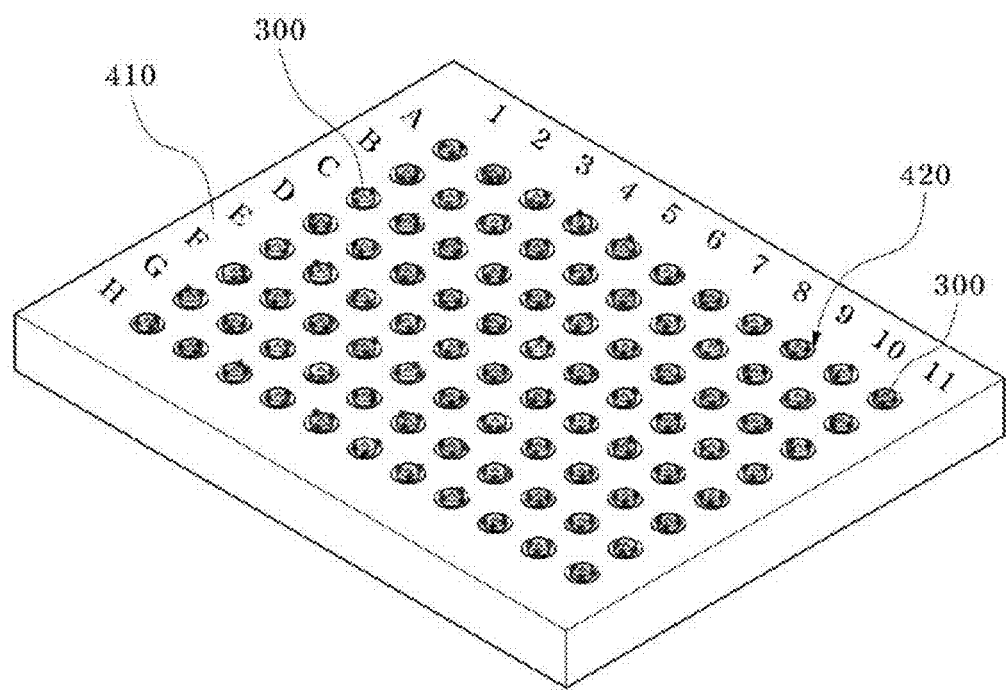
Figure 15:
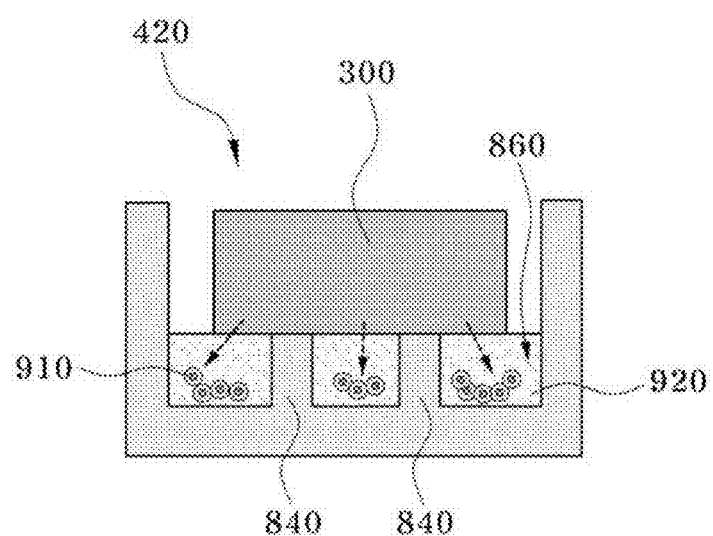

FIG. 14 is a diagram schematically illustrating a process of releasing the target materials of the particles to cause a reaction with the analyte according to an exemplary embodiment of the present disclosure. Referring to a block 250 and FIG. 14, the target materials of the particles 300 are released to react with the analyte 910. As a method of releasing the target materials, for example, a natural release method or a forced release method may be used. In a process of releasing the target materials from the particles 300 as the natural release method according to an exemplary embodiment, referring to FIG. 15, the medium including the analyte 910 is made to contact the particles 300, such that the target materials of the particles 300 can be diffused from the particles 300. The medium 920 may be selected to react with the particles 300, and cause the target materials in the particles 300 to be released from the particles 300 as time elapses. The target materials released from the particles 300 may react with the analyte 910 in the wells 420. In the case of the above-described natural release method, the degrees of reaction of the particles 300 may differ from one another according to the length of time during which the medium 920 including the analyte 910 is in contact with the particles 300. Thus, in comparison with the method of supplying the medium 920 to the plurality of wells 420 by pipetting as described above with reference to FIG. 11, the method of disposing the analyte 910 in the wells 515 of the separately manufactured plate 510 and combining the plate 410 including the wells 420 in which the particles 300 are disposed as described above with reference to FIG. 12 is advantageous. In other words, since the medium 920 including the analyte 910 can be simultaneously supplied to the plurality of encoded particles 300, it is possible to provide substantially the same reaction time.

Figure 16:
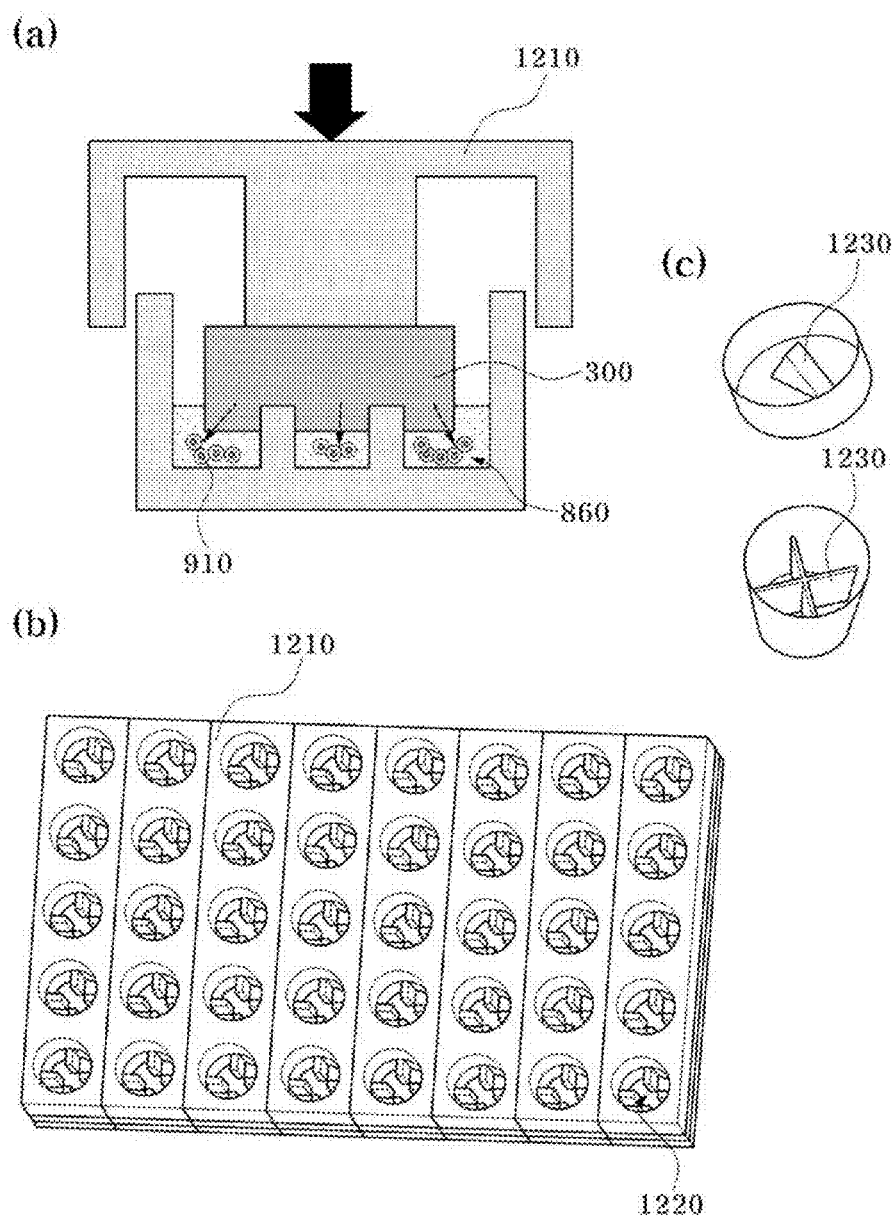

In another exemplary embodiment, referring to (a) of FIG. 16, the process of releasing the target materials from the particles 300 may be performed as the forced release method by grinding the particles 300 using the grinder 1210. The grinder 1210 may grind the particles 300 by, for example, pressure applied from the outside. When the particles 300 are ground, the target materials may be released from the particles 300 and react with the analyte 910 in the wells 420. (b) of FIG. 16 shows an aspect of the grinder 1210 according to an exemplary embodiment of the present disclosure. The grinder 1210 may have a plurality of grinding unit cells 1220 respectively corresponding to the wells 420. (c) of FIG. 16 shows an aspect of the grinding unit cells 1220. The grinding unit cells 1220 may include cutting structures 1230 capable of grinding the particles 300 therein. In the drawing, one column and a cross-shaped column are shown as the cutting structures 1230. However, the cutting structures 1230 are not limited to the drawing and may have various shapes and sizes. Referring back to (b) of FIG. 16, when the forced release method is used, a plate 1210, which is the grinder 1210 having the grinding unit cells 1220 corresponding to the plurality of wells 420 in which the particles 300 are aligned, may be separately prepared. By aligning and attaching the plurality of wells 420 and the plurality of grinding unit cells 1220 to correspond to each other, the particles may be forced to be ground.

Figure 12:
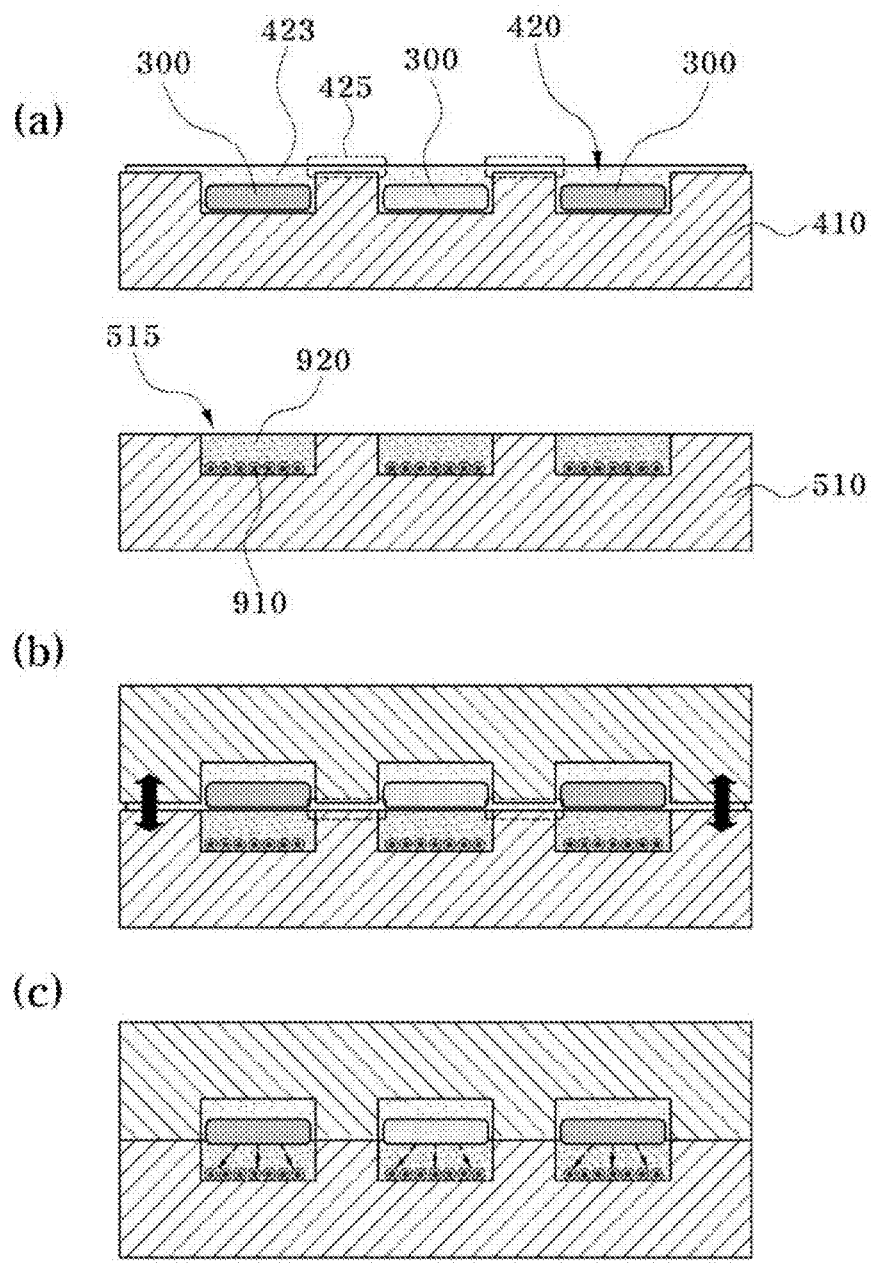

In some exemplary embodiments, the above-mentioned cutting structures 1230 may be installed in the wells 420 having the particles 300 or the wells 515 having the analyte 910 (see FIG. 12). The wells 420 having the particles 300 and the wells 515 having the analyte 910 are aligned and attached to correspond to each other, such that the particles can be ground by the cutting structures 1230. The cutting structures 1230 installed in the wells 420 having the particles 300 or the wells 515 having the analyte 910 may also serve as a marker that aligns the wells 420 having the particles 300 and the wells 515 having the analyte 910. For example, the cutting structures 1230 may be designed with a higher height than the wells 420 or the wells 515 to cover both the wells 420 and the wells 515, such that the wells 420 and the wells 515 can be aligned. The forced release method according to the above-described method may be applied to the natural release method described above with reference to FIG. 14. Thus, the wells 420 having the particles 300 and the wells 515 having the analyte 910 are aligned and attached to correspond to each other, such that both the natural release method and the forced release method can be used.

Figure 17:
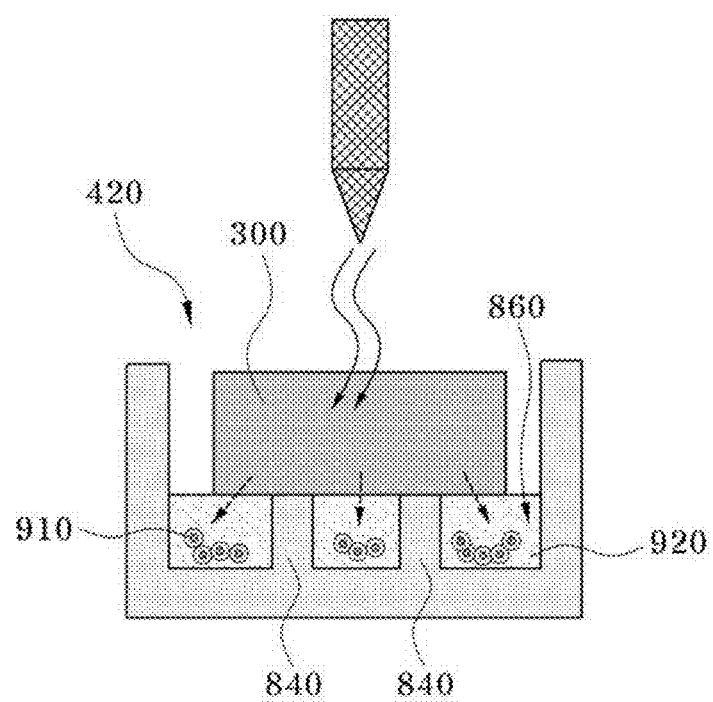

In still another exemplary embodiment, referring to FIG. 17, the process of releasing the target materials from the particles 300 may be performed through a process of heating and destroying at least parts of the particles 300. The process of heating and destroying at least parts of the particles 300 may be performed, for example, using a laser as shown in the drawing. The laser may locally heat parts of the particles 300. The parts locally heated by the laser are melted, such that the target materials can be released from the particles 300. The released target materials may react with the analyte 910 in the wells 420.

In some exemplary embodiments, when the analyte 910 is a biological material such as cells, a process of removing the particles 300 having released the target materials and fixing the analyte 910 may be additionally performed. When the analyte 910 is the biological material such as cells, the target materials reacting with the biological material may be a drug. When the drug is sufficiently released from the particles 300, the ground or destroyed particles 300 may be removed, and a fixation process may be performed to suppress metabolic activities of the biological material. The fixation process may be performed using formaldehyde.

Figure 18:
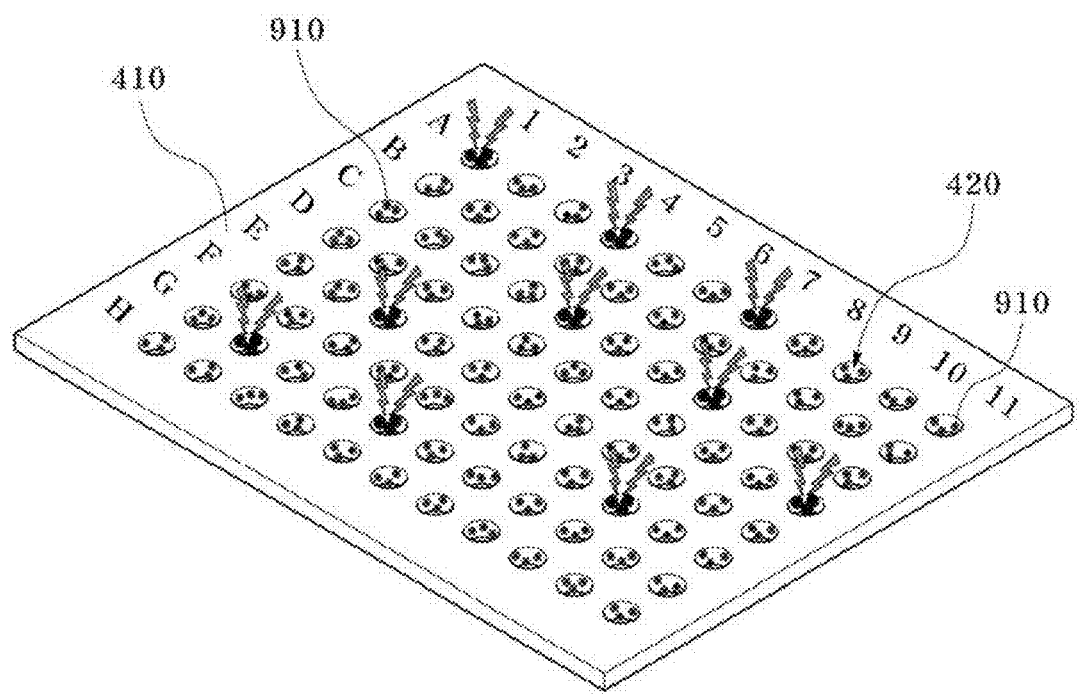

As shown in FIG. 18, by observing whether or not the plurality of various target materials released from the plurality of encoded particles 300 through the above-described process react with the analyte 910 in the wells 420, it is possible to select a specific target material that reacts with the analyte 910. To observe the reaction, a material, for example, which emits light such as fluorescence or phosphorescence when a specific reaction occurs, may be used as an indicator. For example, when the analyte 910 is a drug, it is possible to check whether or not the biological material fixed as described above reacts with the drug by observing a change of the biological material. The reaction may be, for example, an antigen-antibody immune reaction. The codes of the particles 300 disposed in the plurality of wells 420 are decoded as described above, such that a breakdown of the drug included in the plurality of particles 300 can be checked. Thus, it is possible to rapidly know the breakdown of the drug reacting with the biological material.

As described above, an assay method according to an exemplary embodiment of the present disclosure uses an encoded particle-based platform. The platform may be a plate having a plurality of wells. In an assay method according to an exemplary embodiment of the present disclosure, particles including a plurality of target materials may be encoded, and the plurality of encoded particles may be simultaneously provided onto the plate by various forms of pipetting. The plurality of particles provided onto the plate may be disposed or aligned in the plurality of wells of the plate by the self-assembly method in a relatively short time. Also, codes of the plurality of particles disposed in the plurality of wells are decoded, such that breakdowns of the plurality of particles disposed in the respective wells can be checked. In the above-described assay method according to an exemplary embodiment of the present disclosure, a plurality of particles can be economically disposed in a plurality of wells in terms of cost and time, compared to an existing method. The existing method requires a relatively long time because each particle is sequentially disposed in one well by one pipetting operation. Thus, when a large amount of particles need to be disposed in a plurality of wells, the existing method is very disadvantageous in practice. On the other hand, an assay method according to an exemplary embodiment of the present disclosure has an advantage in that, for example, even 100K or more particles can be disposed in the corresponding wells in a short time by one pipetting operation.

In an exemplary embodiment of the present disclosure, a plurality of coded particles including target materials can be economically provided onto a plate for analysis by one pipetting operation. Specifically, using, for example, a digital micromirror device that does not employ a mask, one million or more codes of various kinds can be formed in the particles including the target materials, and the particles including the target materials having the various kinds of codes can be provided onto the plate for analysis by one pipetting operation.

In an exemplary embodiment of the present disclosure, a plurality of coded particles can be disposed in wells of an assay plate by one pipetting operation and the self-assembly method. In other words, the particles having the one million or more codes of various kinds are disposed in the wells of the plate for analysis by the self-assembly method, and can be subjected to high-speed screening through a reaction with a drug. In this way, the process can be economically performed in terms of cost and time, compared to an existing method of pipetting coded particles one by one.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method of selecting a target material reacting with an analyte based on an encoded particle-based platform, comprising the steps of:

preparing a plurality of encoded particles including the target material, the plurality of encoded particles having one or more codes distinguishable from one another corresponding to the target material, wherein the codes distinguish the target material;

preparing a first plate including first wells, providing the plurality of encoded particles onto the first plate by pipetting, and disposing the plurality of encoded particles in the first wells;

preparing a second plate including second wells and disposing the analyte in the second wells;

attaching the first plate to the second plate where the first wells of the first plate and the second wells of the second plate correspond to each other;

decoding the codes of the plurality of encoded particles disposed in each of the first wells;

releasing the target material by diffusing from the plurality of encoded particles via the step of attaching the first plate to the second plate, wherein the target material is released into the second wells and a reaction is caused between the target material and the analyte; and selecting the target material which reacts with the analyte, wherein the step of preparing the plurality of encoded particles comprises:

mixing the target material and a polymer to form a solution in a resin form; and solidifying the solution formed in the resin form to form the encoded particles in which the target material is included in the polymer.

2. A method of selecting a target material reacting with an analyte based on an encoded particle-based platform, comprising the steps of:

preparing a plurality of encoded particles including the target material, the plurality of encoded particles having one or more codes distinguishable from one another corresponding to the target material, wherein the codes distinguish the target material;

preparing a first plate including first wells, providing the plurality of encoded particles onto the first plate by pipetting, and disposing the plurality of encoded particles in the first wells;

preparing a second plate including second wells and disposing the analyte in the second wells;

attaching the first plate to the second plate where the first wells of the first plate and the second wells of the second plate correspond to each other;

decoding the codes of the plurality of encoded particles disposed in each of the first wells;

releasing the target material by diffusing from the plurality of encoded particles via the step of attaching the first plate to the second plate, wherein the target material is released into the second wells and a reaction is caused between the target material and the analyte; and selecting the target material which reacts with the analyte, wherein the step of preparing the plurality of encoded particles comprises:

dissolving the target material in poly-N-isopropylacrylamide (PNIPAAM);

mixing the PNIPAAM and polyethylene glycol-diacrylate (PEG-DA) to produce a composite in a resin form; and solidifying the composite.

3. A method of selecting a target material reacting with an analyte based on an encoded particle-based platform, comprising the steps of:

preparing a plurality of encoded particles including the target material, the plurality of encoded particles having one or more codes distinguishable from one another corresponding to the target material, wherein the codes distinguishe the target material;

preparing a first plate including first wells, providing the plurality of encoded particles onto the first plate by pipetting, and disposing the plurality of encoded particles in the first wells;

preparing a second plate including second wells and disposing the analyte in the second wells;

attaching the first plate to the second plate where the first wells of the first plate and the second wells of the second plate correspond to each other;

decoding the codes of the plurality of encoded particles disposed in each of the first wells;

releasing the target material by diffusing from the plurality of encoded particles via the step of attaching the first plate to the second plate, wherein the target material is released into the second wells and a reaction is caused between the target material and the analyte; and selecting the target material which reacts with the analyte, wherein the step of preparing the plurality of encoded particles comprises:

forming a first polymer layer;

forming a target material layer on the first polymer layer; and forming a second polymer layer sealing the target material layer.

4. The method of claim 3, wherein the step of forming the first polymer layer includes providing and solidifying a fluidic polymer, and the step of forming the second polymer layer includes providing and solidifying the fluidic polymer.

5. The method of claim 3, wherein the step of forming the target material layer includes providing a fluidic polymer including the target material, and solidifying the fluidic polymer.

6. The method of claim 5, further comprising:

mixing the target material and a polymer to form a solution in a resin form on the first polymer layer; and solidifying the solution formed in the resin form.

7. The method of claim 3, wherein the step of forming the target material layer includes:

forming a hydrophilic polymer layer on the first polymer layer; and causing the hydrophilic polymer layer to absorb the target material.

8. The method of claim 3, wherein the step of forming the target material layer includes:

forming a first structure in a form of a wall on the first polymer layer along an edge of the first polymer layer using a hydrophobic polymer;

forming a second structure on a sidewall in the first structure using a hydrophilic polymer; and forming the target material layer in the second structure on the first polymer layer.

* * * * *